(12) United States Patent
Kurozumi et al.

(10) Patent No.: US 6,407,812 B1
(45) Date of Patent: Jun. 18, 2002

(54) LASER BEAM OPTICAL AXIS ADJUSTING MECHANISM IN PARTICLE SIZE DISTRIBUTION MEASURING APPARATUS

(75) Inventors: Takuji Kurozumi; Kazuyuki Ikemoto, both of Miyanohigashi-machi (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 09/548,105

(22) Filed: Apr. 12, 2000

(30) Foreign Application Priority Data

Apr. 16, 1999 (JP) .......................................... 11-108871

(51) Int. Cl.[7] ............................................... G01N 15/02
(52) U.S. Cl. ....................... 356/336; 356/340; 356/343
(58) Field of Search ......................... 356/335, 336–343, 356/73, 399; 250/564, 574, 201.9; 318/632, 636

(56) References Cited

U.S. PATENT DOCUMENTS 4,467,186 A * 8/1984 Gorainick et al. ....... 250/201.9
5,424,834 A * 6/1995 Akedo et al. ................ 356/371
5,737,078 A * 4/1998 Takarada et al. ............ 356/338
6,061,131 A * 5/2000 Igushi et al. ................ 356/336
6,252,658 B1 * 6/2001 Togawa et al. ............. 356/336

FOREIGN PATENT DOCUMENTS

JP        11-83722     * 3/1999

* cited by examiner

*Primary Examiner*—Hoa Q. Pham
(74) *Attorney, Agent, or Firm*—Price and Gess

(57) ABSTRACT

A laser beam optical adjusting mechanism for a particle size distribution measuring apparatus includes a light source to provide a laser beam for irradiating a sample cell and an optical detector unit for receiving an intensity pattern representing the impact of the laser beam on a cell. A mirror assembly is positioned adjacent the light source to reflect the laser beam to irradiate the sample cell. An actuator unit is provided for adjusting the mirror assembly to line an optical axis of the light source with an optical detector. The actuator unit can be automatically driven by a controller and can be of a compact configuration by the use of a pair of lever members that are pivotally supported and respectively driven by actuators.

24 Claims, 12 Drawing Sheets

LASER BEAM OPTICAL AXIS ADJUSTING MECHANISM IN PARTICLE SIZE DISTRIBUTION MEASURING APPARATUS

BACKGROUND OF THE INVENTION

1. Field of the Invention

The present invention relates to a laser beam optical axis adjusting mechanism in a particle size distribution measuring apparatus which is furnished with a light source for irradiating a laser beam onto a sample and an optical detector for receiving the scattered light irradiated on the sample to measure the particle size distribution of the sample based on the intensity pattern of the light scattered over the sample and more particularly to an adjustable mirror to enable a simple and compact design.

2. Description of Related Art

A conventional particle size distribution apparatus for example, as shown in FIG. 12, includes a laser light source for generating a laser beam 71, a condenser lens 72, a cell 73 for accommodating the sample 74, and a light detector 75 for receiving the light scattered by irradiation on the sample 74. The light detector 75 is designed to measure the particle size distribution of the sample based on the intensity pattern of the light which has been scattered as it passes through the sample.

In the particle size distribution apparatus described above, obtaining an accurate coincidence of an optical axis of the laser beam with a center of the optical detector 75 is important in measuring the particle size of the sample to any acceptable level of precision. The optical axis of a laser beam can be offset from the center of the optical detector 75 due, for example, to thermal stress of the laser light source 71, thermal stress of the bench base (illustration omitted) that is provided with the cell 73, the condenser lens 73 and the optical detector 75 or the like, or due to a change of the mounting position at the time of the replacement of the cell 73. It is a general practice that the optical axis adjustment is generally performed on each occasion of measurement of the particle size.

To cope with the above situation, though illustration is omitted, there has been a practice to provide four light receiving elements such as photo-diodes at a central part of the optical detector 75, and, prior to the measurement, to align the optical axis by moving the optical detector 75 in the directions of X and Y axes so as to make the size of the intensity signals outputted from the four light receiving elements equal.

In order to move the optical detector 75 in the direction of the X and Y axes, ordinarily there are used two separate actuators 76, 77 such as a piezoelectric element, stepping motor, etc. The optical detector 75 is called a ring detector or a light receiving element comprising a plurality of photodiodes formed in an arc shape and arrayed in a sector configuration on the plate surface to form a large plate-like member. The optical detector 75 is at a position on the furthest side of the cell 73 and distant from the laser light source 71. For this reason, in order to secure a sufficient shift amount necessary for making an optical axis adjustment, a large space is required to be provided in the apparatus, with the consequence of a large size requirement for the optical axis adjusting mechanism, a complexity of construction, and an alignment requirement of a high cost.

The prior art is still seeking improvements in this field including requirements to render the measurement apparatus in a compact configuration.

SUMMARY OF THE INVENTION

The prevent invention provides a laser optical axis adjusting mechanism having a simple and compact construction at low cost, with an entirely unique style of optical axis adjustment from that of conventional systems.

In order to attain the above objects, the present invention is characterized by providing the laser beam optical axis adjusting mechanism with a mirror member for reflecting light irradiated from the laser light source and directing it towards an optical detector, an actuator unit for changing an angle of the mirror surface around an axial axis in two-dimensional directions, and an actuator controlling unit for bringing the optical axis of the laser beam which is reflected on the mirror face into agreement with a center and of the above optical detector. The actuator unit can include a support base for the mirror member and a pair of actuator members for moving the support base in two dimensions. The support base can be mounted with a universal coupling and each actuator member can include lever members that are integrally connected to a support structure with L-shaped slits.

The optical axis of the laser beam can be significantly modified in angle by a slight angular change of the mirror position, and since the change of the mirror angle for optical axis alignment can be satisfied by only a small amount of movement, especially the nearer the mirror is positioned to the laser light source, a small mirror is effective for reflecting the laser beam. Accordingly, it is possible to constitute the entire optical axis adjusting mechanism including the actuator, at a low cost, and in a compact design.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a compact and inexpensive optical axis alignment device for a particle size distribution measuring apparatus.

Figure 1:
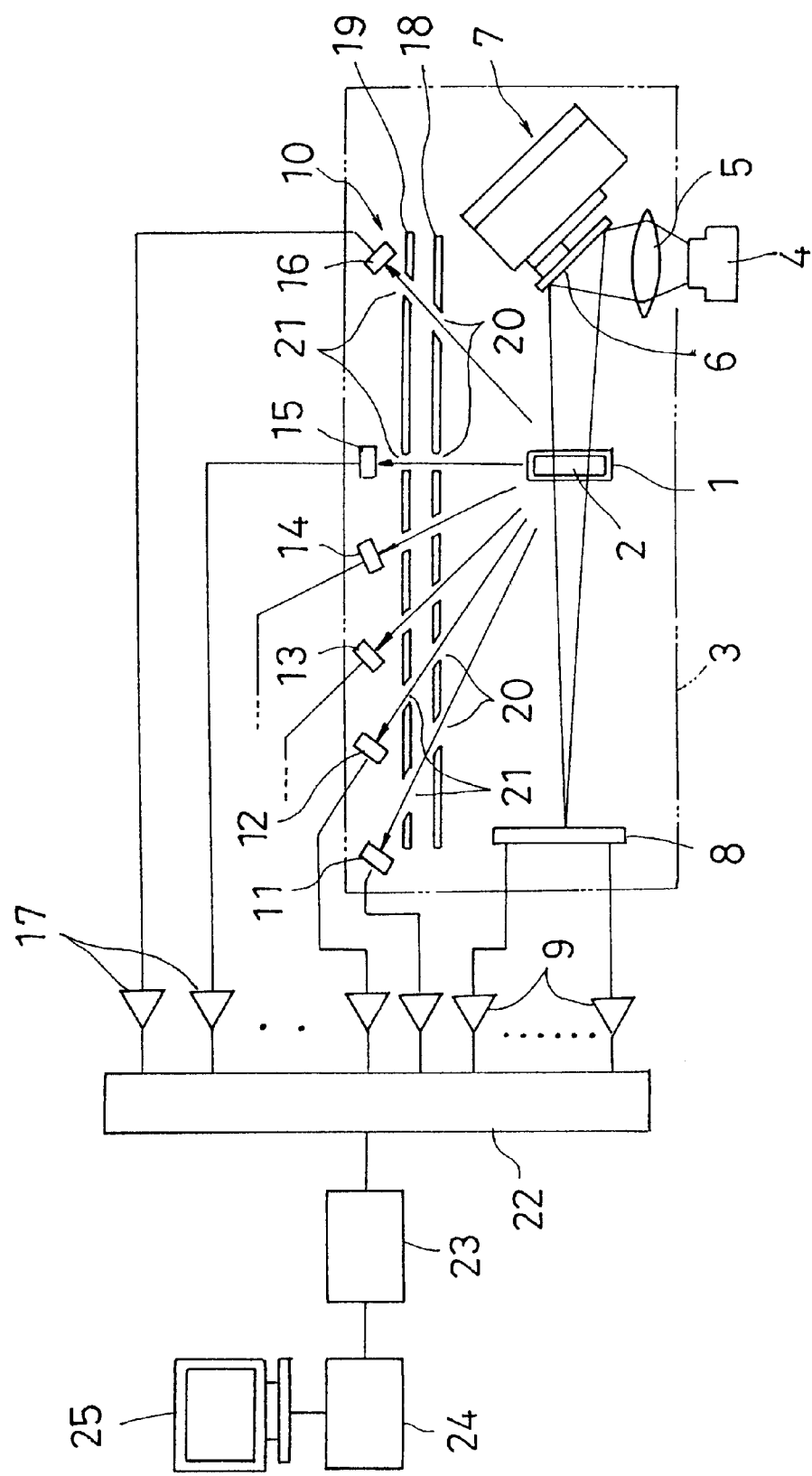
FIG. 1 is a schematic view of a particle size distribution measuring apparatus of the present invention.

Hereinafter, an embodiment of the present invention is explained with reference to the drawings. FIG. 1 shows schematically the elements of a laser diffraction type particle size distribution measurement apparatus. In FIG. 1, a flow cell 1 comprises a transparent container for accommodating a sample 2 in a form of a group of particles which are the subject of measurement dispersed in a dispersing medium. The flow cell 1 is supported in elevation on the upper surface of an optical bench base 3 shown in dotted lines and the sample can be positioned in a static or dynamic (e.g., flow through) mode as known in the art.

A laser light source 4 emits a laser beam in a horizontal direction. A condenser lens 5 condenses the divergent laser beams initially emitted from the laser light source 4 in order to form them on the sample 2. A mirror member 6 projects by reflection the converging laser beams which have passed through the condenser lens 5 (hereinafter to be referred to as condensed laser beams) to the flow cell 1 by bending the beams by 90 degrees. The mirror 6 is held by an automatically controlled laser optical axis adjusting mechanism 7.

Figure 2:
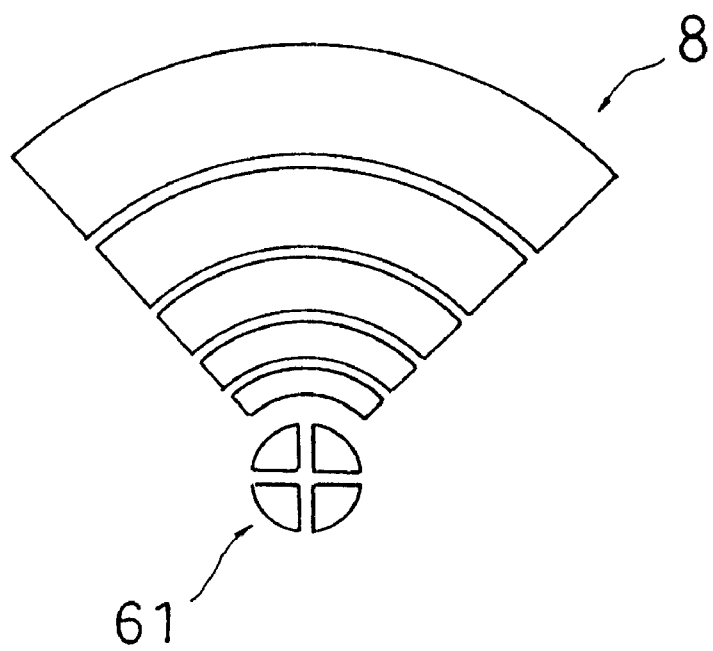
FIG. 2 is an illustration of an arrangement of a light detector and a transmitted light detector for optical axis adjustment.
Figure 3:
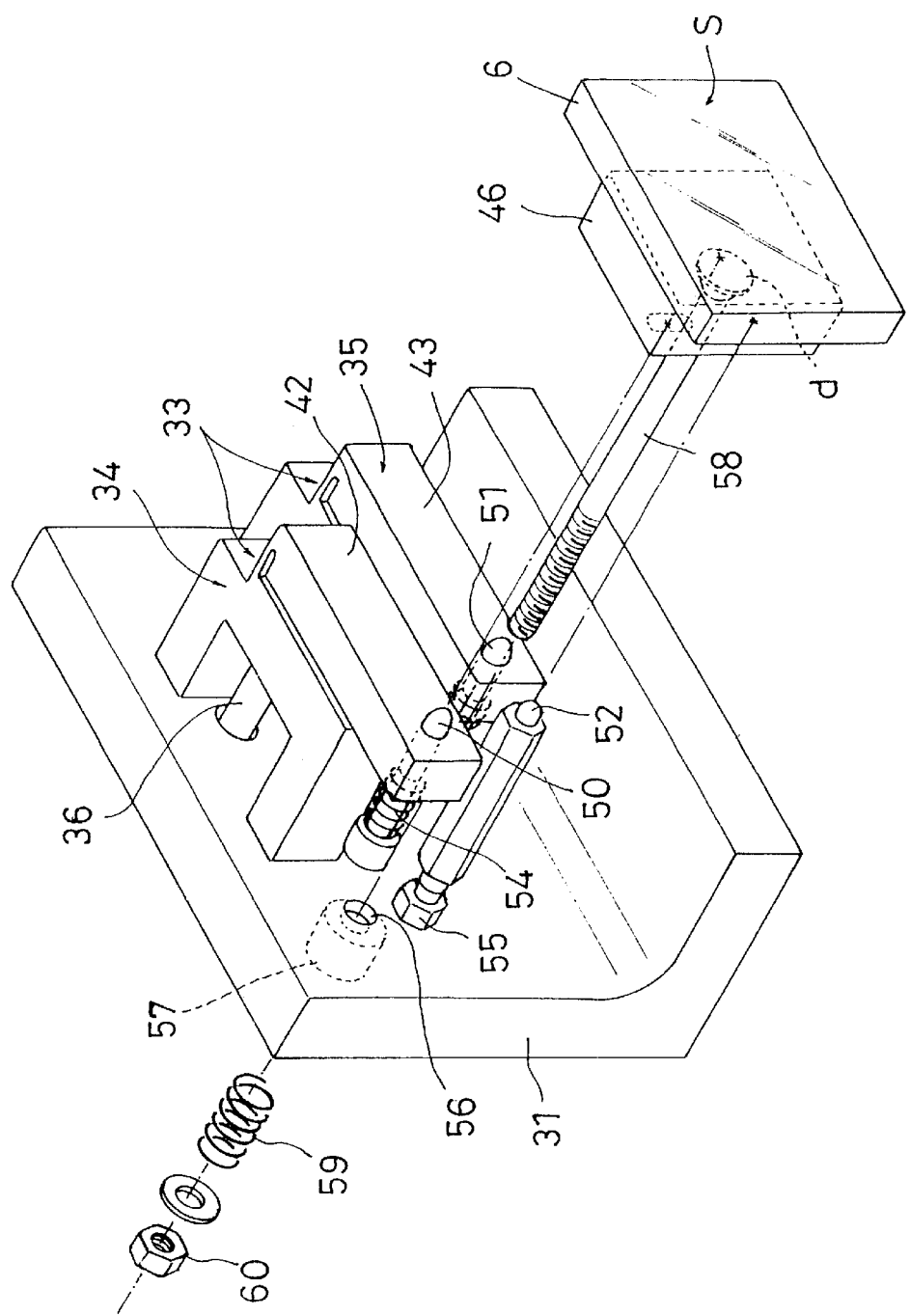
FIG. 3 is a partial exploded perspective view of a laser optical axis adjusting mechanism.
Figure 4:
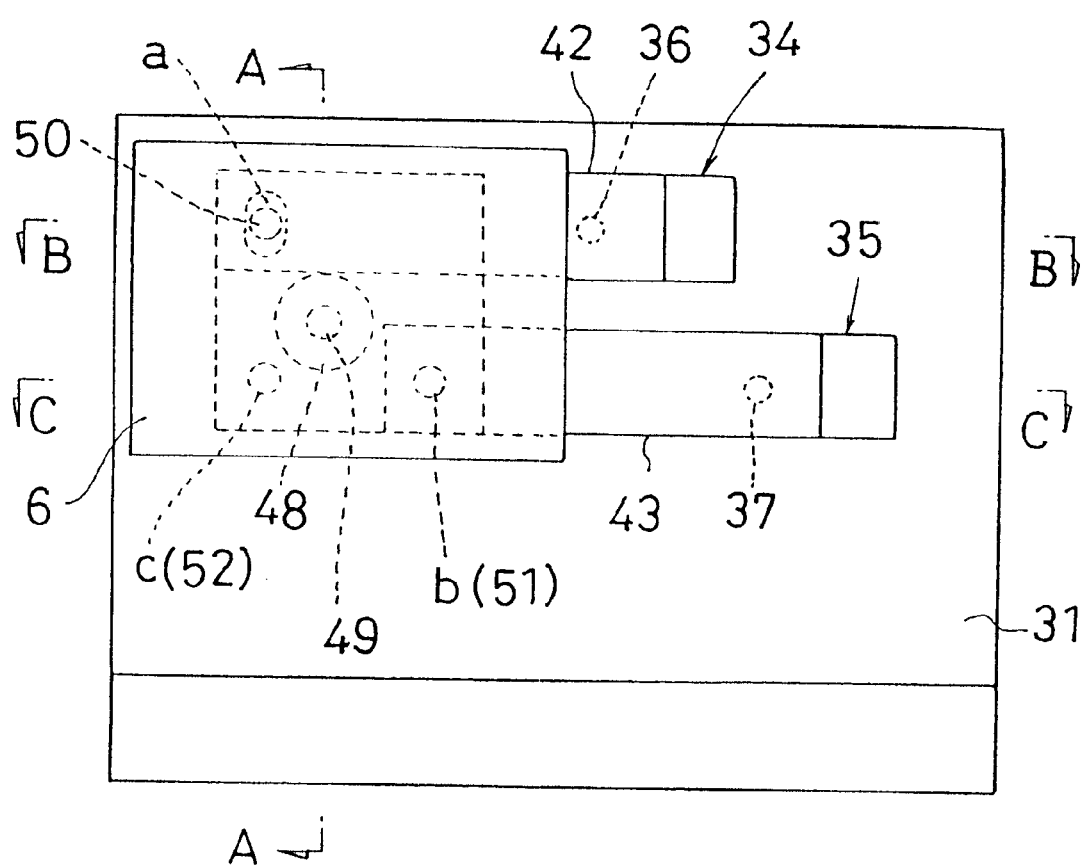
FIG. 4 is a front elevation view of a laser optical axis adjusting mechanism.
Figure 5:
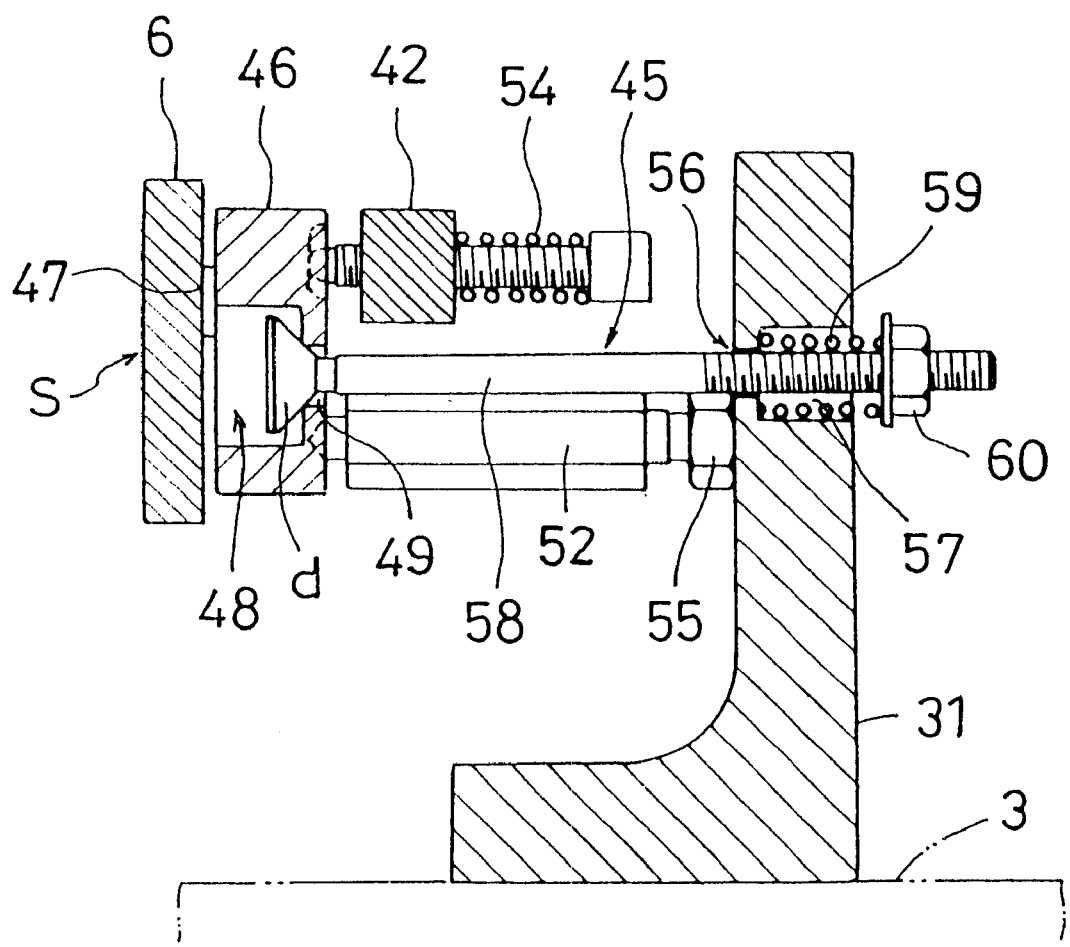
FIG. 5 is a cross sectional view taken along the A—A line in FIG. 4.
Figure 6:
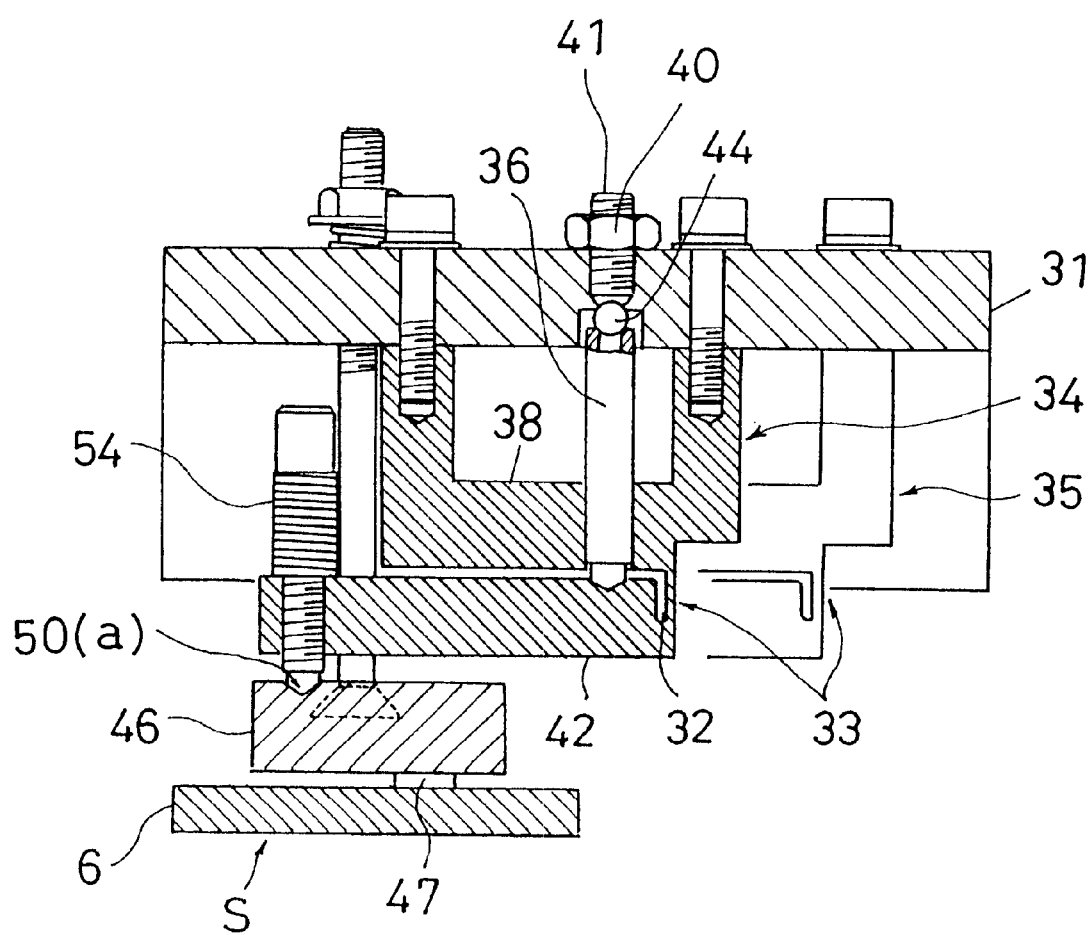
FIG. 6 is a cross sectional view taken along the B—B line in FIG. 4.
Figure 7:
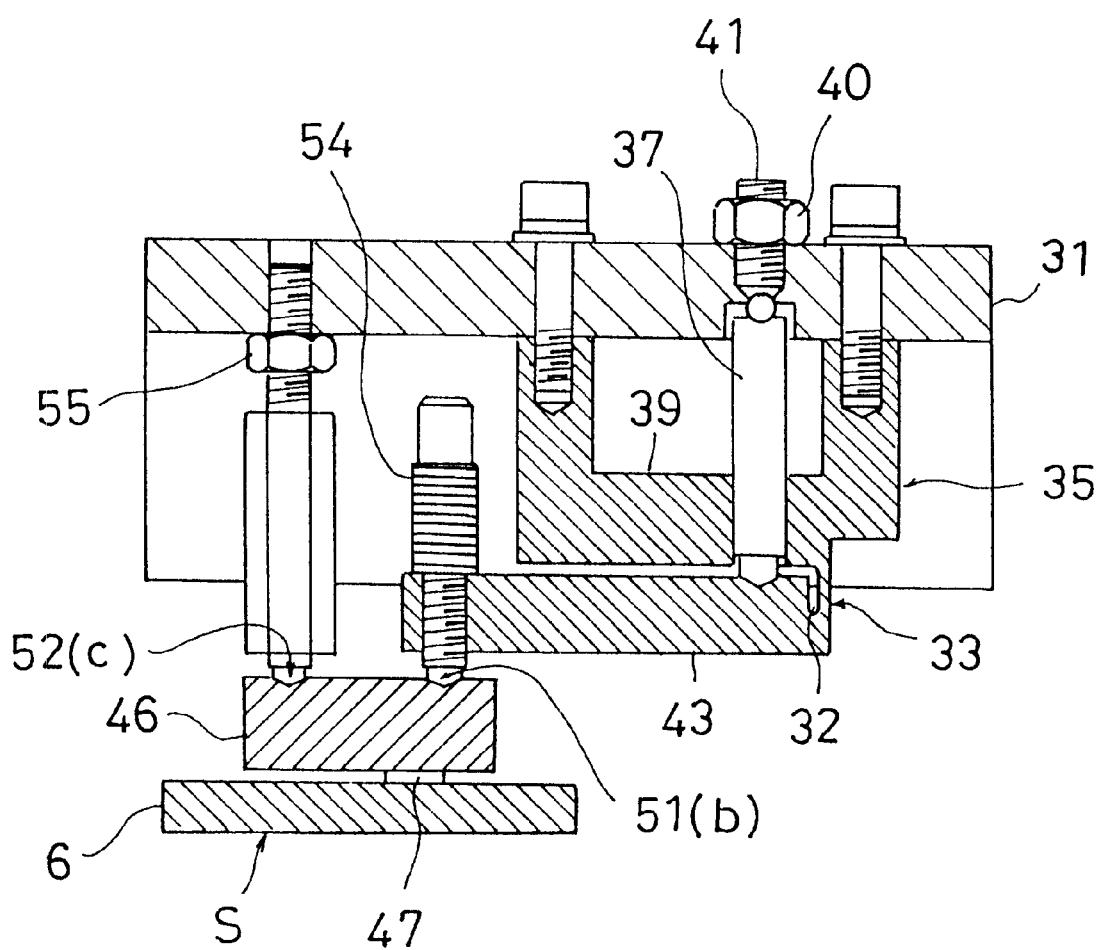
FIG. 7 is a cross sectional view taken along the C—C line in FIG. 4.

A light detector 8 (such as a ring detector) is provided in a position for the condensed laser beams which have passed through the flow cell 1 to focus. This light detector 8 is, as shown in FIG. 2, made by arranging concentrically a plural number of photosensors having light receiving faces in an arc form or ring form at different radii centering on the optical axis of the condensing laser beams. The light detector 8 receives the scattered/diffracted rays at a relatively small angle for each divergent angle of the diffracted or scattered condensed laser beams after contact with the particles in the flow cell 1, and measures their light intensity. Preamplifiers 9 can amplify the output of each photosensor of the light detector 8.

Adjacent the flow cell 1, there is provided a group of light detectors 10 for receiving any wide angle scattered light, thereby detecting individually the respective scattering angles, so as to detect light which has been scattered/diffracted at relatively large angles from the condensed laser beams as they are diffracted or scattered by the particles contained in the flow cell 1.

This group of light detectors 10, for wide angle scattered light, comprises a plurality of photosensors 11–16 which are provided at angles which differ significantly from that of the light detector 8. These photosensors can detect the scattered light at predetermined angles in excess of the predetermined angle of the light detector 8. Namely, the photosensors 11–14 detect the frontward scattered light, the photosensor 15 detects the side scattered light, and the photosensor 16 detects the backward scattered light, respectively.

The elements 17 are preamplifiers for amplifying the outputs of the respective photosensors 11–16. Two light shield plates 18 and 19 are provided in an upright position relative to the surface of the optical bench 3 and in a parallel arrangement with each other, on the front side of the light detector group 10, namely on the front side of the respective photosensors 11–16, or more particularly, on the light incident side.

These light shield plates 18, 19 have a plurality of openings or apertures for passing only the scattered rays of specified scattering angles to the photosensors 11–16, e.g., slits 20, 21, respectively, by the procedures of etching or the like, wherein, for example, the left side initial apertures of the slits 20, 21 are aligned with photosensor 11 for detecting the frontward scattered light are not necessarily of the same shape or size as the other slits but their mutual positions are set so as to have only the scattered light of a predetermined scattering angle out of the frontward scattered light from the flow cell 1 to be incident on the photosensor 11. The relationship in this respect of the other apertures are the same with respect to the slits 20, 21 to align with other photosensors 12–16.

A multiplexer 22 sequentially takes in the outputs from the preamplifiers 9, 17 and sequentially sends them out to the A/D converters 23. A controller unit including a computer 24 such as an operation processor in which the output of the A/D converter is to be inputted is provided.

The computer 24 stores a program for processing the outputs of the light detector 8 and the photosensors 11–16 (digital data relating to light intensity) which have been converted to the digital signals based on the Fraunhofer diffraction theory or Mie scattering theory to obtain a particle size distribution of the group of particles as known in this art. A color display 25 displays the operation results and other user features.

In the particle size distribution measuring apparatus as described above, the condensed laser beams irradiated on the sample 2 in the flow cell 1 are diffracted or scattered by the particles in the flow cell 1, and rays having relatively small scattering angles from the diffracted or scattered rays are focused for image-forming on the light detector 8.

In this case, the photosensors on the outer periphery side of the light detector 8 receive those rays having large scattering angles, and the photosensors on the inner periphery side receive the rays having small scattering angles. Accordingly, it follows that the light intensity of detection by the outer periphery side reflects the amount of the particles having smaller particle sizes, and the light intensity of detection by the inner periphery side reflects the amount of the particles having larger particle sizes. The light intensity detected by the respective photosensors is converted to an analog electric signal, and further inputted to the multiplexer 22 through the preamplifiers 9.

On the other hand, of the condensed laser beams diffracted or scattered by the particles mentioned above, the rays having a relatively large scattering angles are restricted by the slits 20, 21 formed respectively on the light shielding plates 18, 19 and only those scattered rays having specified scattering angles are incident respectively on the photosensors 11–16, and their light intensity distributions are measured.

In this case, the scattering rays from particles of a larger particle size are detected in order of the photosensors 11–14 for frontward scattered light, photosensor 15 for side scattered light, and photosensor 16 for rearward scattered light. The light intensity detected by each of these photosensors 11–16 is converted to an analog electric signal, and further inputted to the multiplexer 22 through the preamplifier 17.

In the multiplexer 22, the measuring data from the light detector 8 and photosensors 11–16, i.e., analog electric signals, are taken in sequentially in a predetermined order, and converted into direct current signals, which are sequentially converted into digital signals by an A/D converter 23, and further inputted into a computer 24, wherein the light intensity data in the unit of each diffraction angle obtained respectively by the light detector 8 and photosensors 11–16 are processed on the basis of the Fraunhofer diffraction theory or Mie scattering theory, and the results of said processing are displayed on the color display.

The light intensity distribution of the scattered rays in the range of larger particle sizes is measured by the light detector 8, and the light intensity distribution of the wide angle scattered rays in the range of smaller particle sizes is measured by the photosensors 11–16, and the outputs of these light detector 8 and the photosensors 11–16 are processed in the computer 24, so that a particle size distribution in the group of sample particles can be obtained over a broad range from ones of a relatively large particle size to ones having a fine particle size.

Next, the details of the laser optical axis adjusting mechanism 7 are explained based on FIG. 3–FIG. 7. In FIGS. 3–7, an adjusting base 31 is provided upright on the optical bench base 3, having mirror adjusting brackets 34, 35 which are equipped with the hinge members 33 formed by L-letter shaped slits 32 to permit pivotal movement, in two stages of upper and lower positions with a slight displacement of positions in the left and fight directions to provide X and Y adjustment of the mirror 6 as will be explained.

The parts 36, 37 are actuators held by fixed side members 38, 39 on the mirror adjustment brackets 34, 35 (e.g., piezoelectric resistor element (PXT) which may be further replaceable by a stepping motor of the like). These actuators are provided between an adjusting screw 44, see FIG. 6, with a lock nut 40 screw fitted to the above adjusting base 31 and the base side of the movable side members 42, 43 of the mirror adjusting brackets 34, 35, through a ball 44. The actuator 36, 37 can be driven to extend and retract along their longitudinal lengths and the pivoting arrangement with the hinge member permits a lever arrangement to multiply the applied displacement to the mirror member 6 when applied at a distal end position.

The member 45 is base holding unit for holding approximately a central part of the mirror support base 46. It is provided in a position which is slightly separated from the free end of the movable side or lever members 42, 43 on the lower side to the above adjusting base 31, with a mirror 6 being held by bonding to a mirror base 46 through a spacer 47 under a condition to keep the mirror face M perpendicular.

Furthermore, on this mirror support base 46 there is formed a recess of a counter bore 48 which is open on the mirror holding face side with a through hole 49. On the face part of the opposite side to the mirror holding face side, on the positions opposed to the free ends of the movable side members 42, 43 of the mirror adjusting brackets 34, 35 and on a position slightly distant from the free end of the lower side movable side member 43, respectively, there are formed three pin receiving recesses a, b, c in a manner to surround the above counter bore recess 48, with the pin receiving recess a thereof formed in a long groove in the perpendicular direction.

At the free ends of the movable side members 42, 43, there are screw fitted adjusting pins 50, 51 whose tips are screwed in the pin receiving recesses a, b. The adjusting base 31 includes a fulcrum pin 52 for engaging at a tip end into the pin receiving recess c. The fulcrum pin 52 is screw fitted, so that, by adjusting the screw to advance positions of the adjusting pins 50, 51, further, or by the operation of the actuators 36, 37, the fitting angle of the mirror base 46 or the fitting angle of the mirror 6 can be changed.

Based on a first axial line connecting the tips between the adjusting pin of one side 50 and the fulcrum pin 52 and a second axial line connecting the tips between the adjusting pin of the other side 51 and the fulcrum pin 52, the axial lines are positioned to change the angle of the mirror 6, or the mirror face M, around the respective axial lines in a two-dimensional direction, of which the adjusting pins 50, 51 are those for initially changing the angle of the mirror face M during construction, and the actuators 36, 37 are used subsequently for making fine calibration adjustments of the mirror face M automatically by the control unit or means 53 (ref FIG. 8) so as to bring the optical axis of the condensed laser beam which is reflected on the mirror face M into accord with the center of the light detector 8.

Compression springs 54, and lock nuts 55, are respectively used for the initial position fixation of the adjusting pins 50, 51 and the fulcrum pin 52.

The above base holding unit 45 holds the mirror base 46 in a manner to draw it toward the adjusting base 31 side and to force and stop the mirror base 46 against the three pins 50–52, wherein the through-hole 49 of the mirror base 46, concentric through-hold 56, and a recess of counter bore 57 are formed into an adjusting base 31, and a base holding bolt 58 having a plate shaped head d is positioned in the counter bore recess 48 and thrust through the through holes 49, 56 so as to stop it around the through hole 49. A nut 60 is screwed in through the compression spring 59 to the thrusting end of the base holding bolt 58.

The plate form head d of the base holding bolt 55 is conically sloped around the through hole 49 to enable the mirror base 46 to be free to change its position relative to the plate form head d, namely, to have the mirror base 46 held on the adjusting base 31 through a universal link structure, and further, as the mirror base 46 is constituted to be movable in a separate direction to the adjusting base 31, at the time of the angle change of the mirror face M by the above adjusting pins 50, 51 or the actuators 36, 37, the mirror base 46 can be smoothly subjected to a position change around the universal link structure or coupling by the plate form head d, without being accompanied by distortion.

Figure 8:
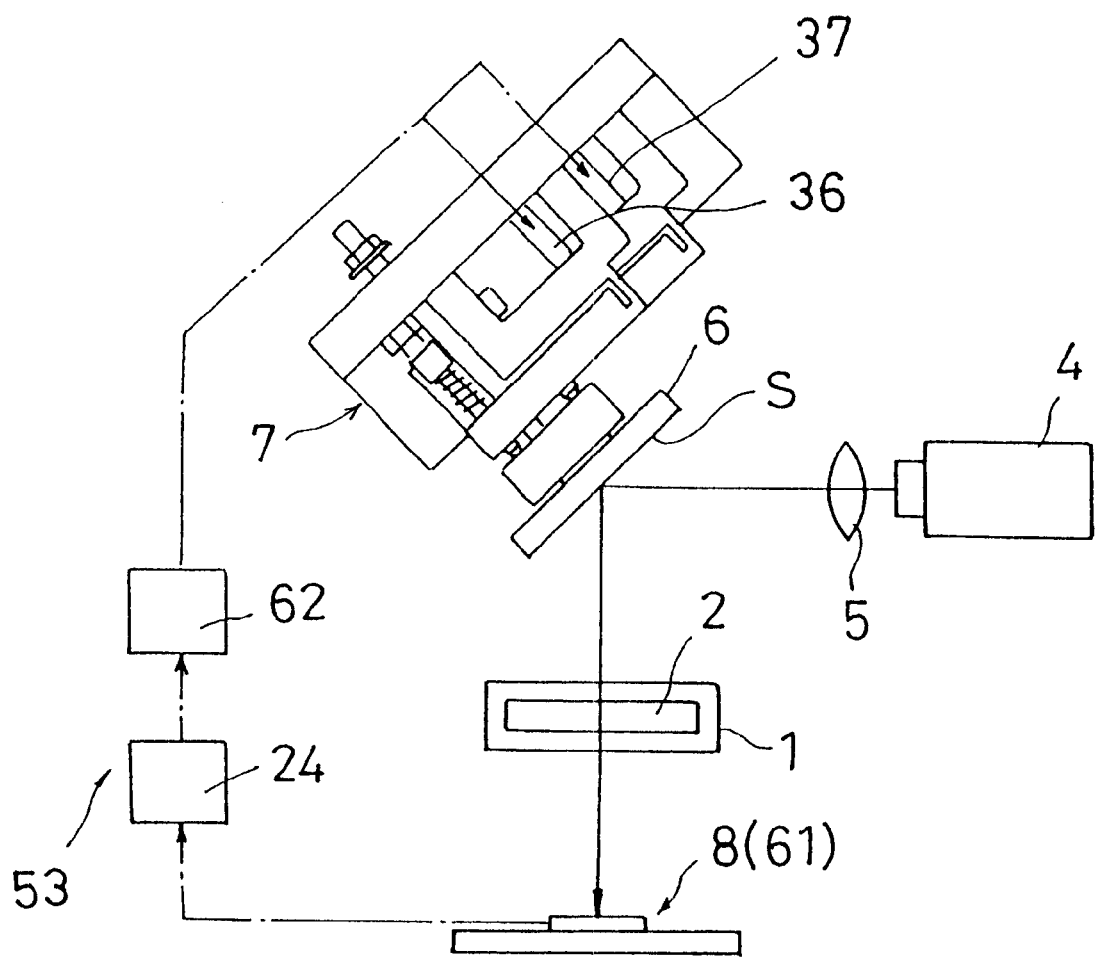
FIG. 8 is a schematic view of an actuator control unit.

On the other hand, the above actuator control unit 53 comprises, as shown in FIG. 2 and FIG. 8 includes target light detectors 61 disposed around the center of optical axis of the light detector 8 (e.g., check pattern of four light receiving elements) for optical axis adjustment and a controller 62 for controlling the operation of the actuators 36, 37 based on the control signals issued from the computer 24.

In particular, by operating the actuators 36, 37 based on control signals inputted from the above computer 24 to the controller 62, the mirror face M or the fitting angle of the mirror 6 is adjusted minutely so that the condensed laser beams which are reflected on the mirror face M are directed to the center of the light detector 8, i.e., so that the light receiving intensity by the above target light detectors 61 become nearly equal. This optical axis adjustment to make the optical axis of the condensed laser beams agree with the center of the light detector 8 is automatically carried out as a calibration procedure prior to the commencement of a measurement cycle of the measurement of particle sizes with the particle size distribution measuring apparatus.

According to the laser optical axis adjustment mechanism 7, because the actuators 36, 37 are disposed on the base side of the movable side members 42, 43, the mirror 6 can be substantially allowed to change its angle by the operation of a slight movement amount of the actuators 36, 37, which is magnified by the respective lever arm or length of the side members 42, 43 and the optical axis of the condenser laser beam can be significantly changed in angle by only a slight angle of the mirror 6, hence the actuators 36, 37 can be of a slight operation amount and a low priced configuration.

In addition, as the mirror 6 is disposed at a position near the laser light source 4, the mirror 6 for reflecting the condensed laser beam can be of a small size, and moreover, as the means for optical axis adjustment per se has a simple constitution of slightly moving the mirror base 46, the whole of the optical axis adjustment mechanism 7 including the actuators 36, 37 can be constructed at low cost in a compact manner.

Figure 9:
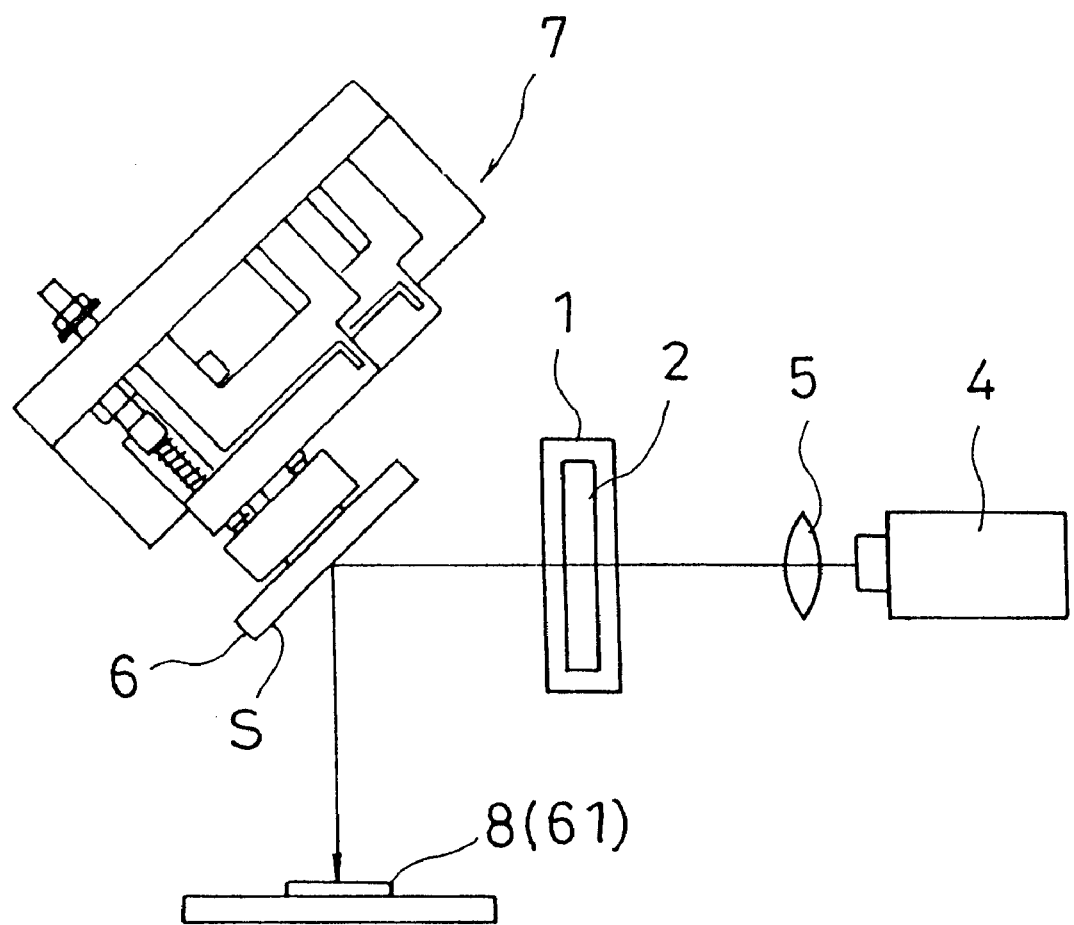
FIG. 9 is a schematic view of a particle size distribution measuring apparatus according to a second embodiment with a different mirror arrangement.

Moreover, as described above, when the mirror 6 is disposed by positioning it close to the laser light source 4, the condensed laser beam can be reflected by a proportionately smaller mirror 6 to give convenience, but this is not necessarily an essential factor since the mirror 6 may be disposed between the flow cell 1 and the light detector 8 as shown, for example, in FIG. 9.

Figure 10:
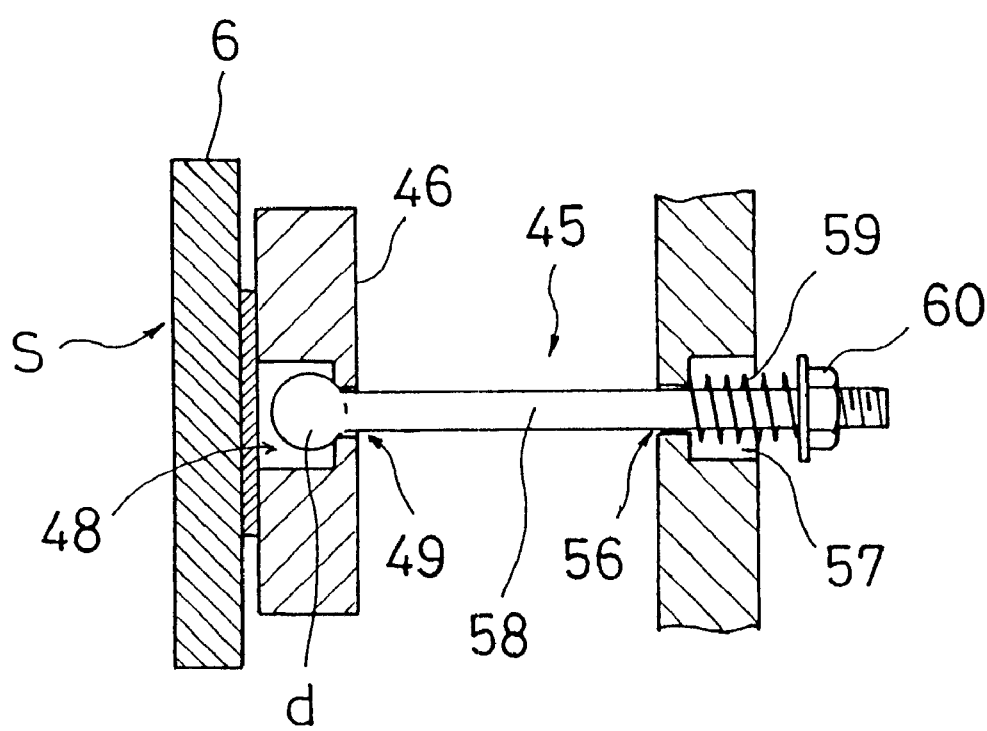
FIG. 10 is a cross sectional view showing a third embodiment of a universal connecting structure.
Figure 11:
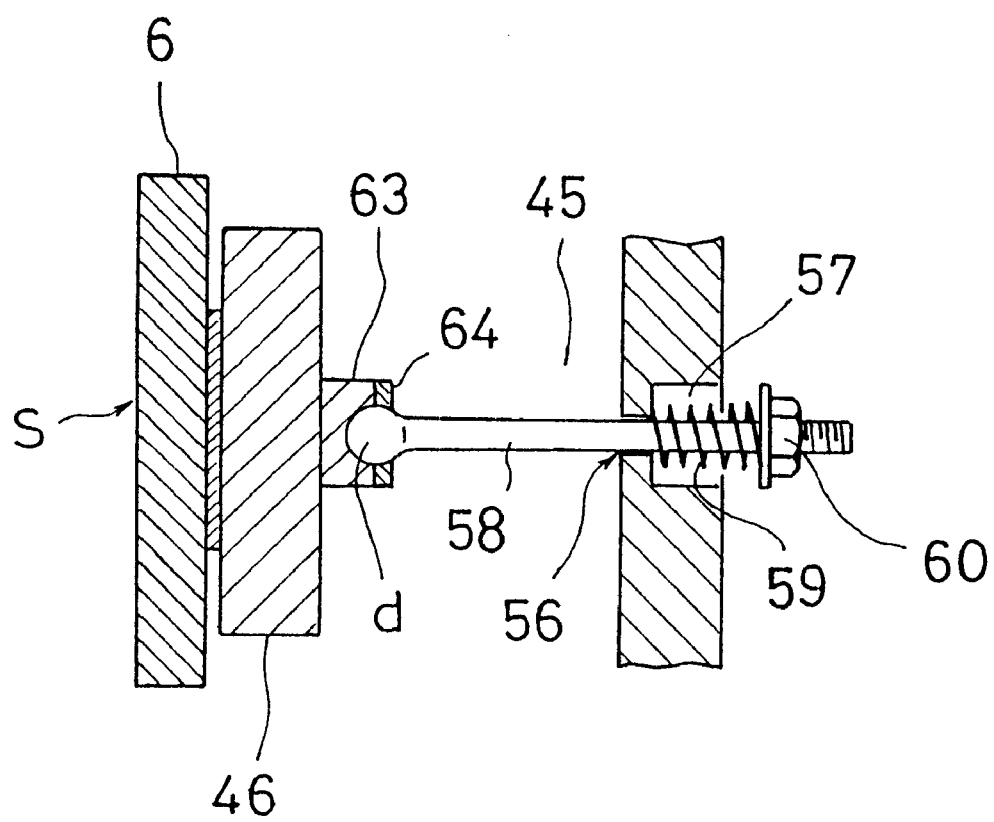
FIG. 11 is a cross sectional view showing a fourth embodiment of a universal connecting structure.
Figure 12:
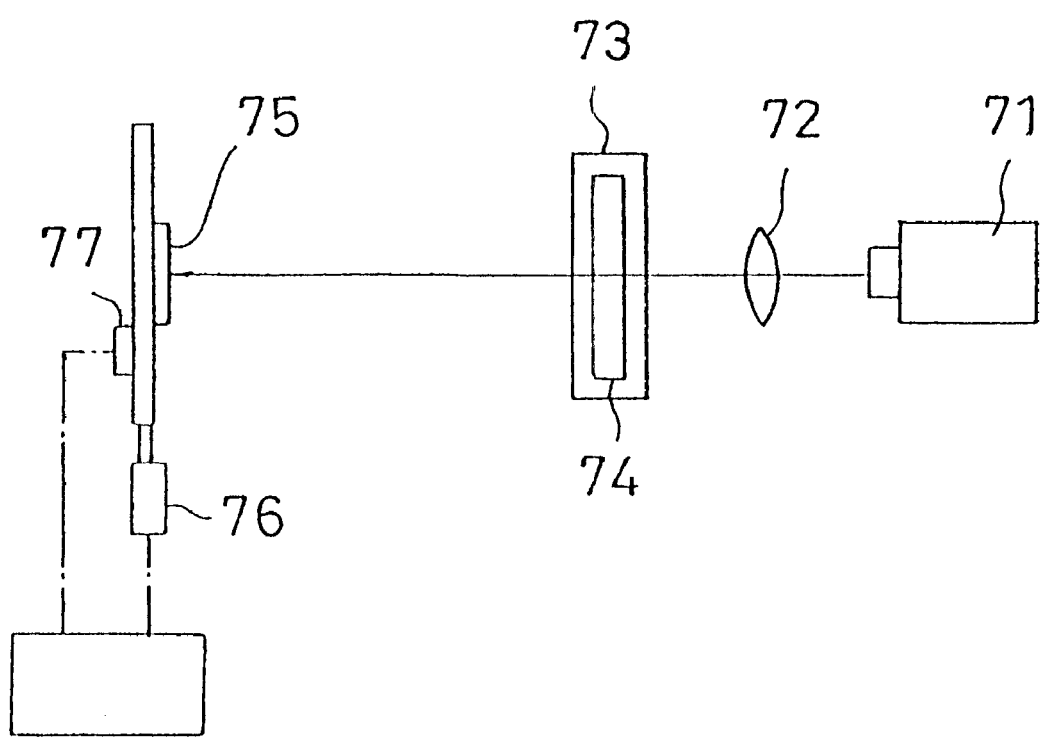
FIG. 12 is a schematic view showing apparatus for adjusting a laser beam axis in a conventional particle size distribution measuring apparatus.

In the present embodiment, there is arranged a base holding unit 45 with the head part d of the base holding bolt 55 formed into a plate form so as to have the mirror base 46 held by a universal linking structure, but as shown in FIG. 10, the bolt head d may be configured in a universal linking structure with the bolt head d made in a spherical form without forming the counter bore recess 48 and the through hole 49 on the mirror base 46. As shown in FIG. 11, a receiving member 63 and a pressing or locking member 64 of the spherical member head d may be provided on the mirror base 46 alternatively to constitute a universal linking mechanism.

Those skilled in the art will appreciate that various adaptions and modifications of the just-described preferred embodiments can be configured without departing from the scope and spirit of the invention. Therefore, it is to be understood that, within the scope of the appended claims, the invention may be practiced other than as specifically described herein.

What is claimed is:

1. In a compact particle size distribution measuring apparatus having a laser beam optical axis adjusting mechanism wherein a light source provides a laser beam for irradiating a sample and an optical detector unit receives an intensity pattern representing the impact of the laser beam on the sample, the improvement comprising:
   a flow cell for receiving the sample;
   a mirror member positioned in front of the light source to reflect the laser beam to irradiate the sample positioned at one side of the light source;
   an actuator unit for adjusting the mirror member to align an optical axis with the optical detector unit; and
   a condenser lens provided between the flow cell and the light source to focus the laser beam on the optical detector.

2. The laser beam optical axis adjusting mechanism of claim 1 further including a controller for automatically driving the actuator unit to align the laser beam with an optical axis.

3. The laser beam optical axis adjusting mechanism of claim 2, further including a target detector unit on the optical axis for receiving the laser beam from the mirror member and connected to the controller to provide a measurement of the position of the laser beam relative to the target detector.

4. The laser beam optical axis adjusting mechanism of claim 3 wherein the actuator unit includes a support base for the mirror member and a pair of actuator members for moving the support base for the mirror in two dimensions to align the laser beam on the optical axis.

5. The laser beam optical axis adjusting mechanism of claim 4 wherein the actuator unit includes lever members connected adjacent distal ends to the support base and pivotally mounted at the ends adjacent the respective actuator members.

6. The laser beam optical axis adjusting mechanism of claim 5 wherein the actuators are piezoelectric resistor elements.

7. The laser beam optical axis adjusting mechanism of claim 5 wherein the lever members are integrally connected to a support structure with L-shaped slits permitting movement.

8. The laser beam optical axis adjusting mechanism of claim 5 further including a base holding unit movably connecting the support base to permit the lever members to rotate the support base about the base holding unit.

9. The laser beam optical axis adjusting mechanism of claim 8 wherein the base holding unit has a conical end and the support base has a receptacle for receiving the conical end.

10. The laser beam optical axis adjusting mechanism of claim 8 wherein the base holding unit has a spherical end and the support base has a receptacle for receiving the spherical end.

11. In a compact particle size distribution measuring apparatus having a laser beam optical axis adjusting mechanism wherein a light source provides a laser beam for irradiating a sample cell and an optical detector unit receives an intensity pattern representing the impact of the laser beam on the sample including an optical detector mounted on a side of the sample cell opposite from the light source, the improvement comprising:
   a mirror assembly positioned, adjacent the source light, to reflect the laser beam to irradiate the sample cell, including an adjusting base, a mirror member and a universal link structure connecting the mirror member to the adjusting base;
   an actuator unit for adjusting the mirror assembly to align an optical axis of the light source with the optical detector, and
   a controller for automatically driving the actuator unit to align the laser beam with the optical axis.

12. The laser beam optical axis adjusting mechanism of claim 11 wherein the actuator unit includes at least one pivotally supported lever member for driving the mirror assembly.

13. The laser beam optical axis adjusting mechanism of claim 12 further including an actuator for rotating the lever member about its pivotal support.

14. The laser beam optical axis adjusting mechanism of claim 11 wherein the actuator unit includes a support base for the mirror assembly and a pair of actuator members for moving the support base for the mirror assembly in two dimensions to align the laser beam on the optical axis.

15. The laser beam optical axis adjusting mechanism of claim 14 wherein the actuator unit includes lever members connected adjacent distal ends to the support base and pivotally mounted at the ends adjacent the respective actuator members.

16. The laser beam optical axis adjusting mechanism of claim 15 wherein the actuators are piezoelectric resistor elements.

17. The laser beam optical axis adjusting mechanism of claim 15 wherein the lever members are integrally connected to a support structure with L-shaped slits permitting movement.

18. In a compact particle size distribution measuring apparatus having a laser beam optical axis adjusting mechanism wherein a light source provides a laser beam for irradiating a sample cell and an optical detector unit receives an intensity pattern representing the impact of the laser beam on the sample including an optical detector mounted on a side of the sample cell opposite from the light source, comprising:

a mirror assembly positioned, adjacent the light source, to reflect the laser beam to irradiate the sample cell; and an actuator unit for adjusting the mirror member to align an optical axis of the light source with the optical detector, the actuator unit includes a support base with a universal coupling member for mounting a mirror member, a pair of actuator members for moving the support base for the mirror member in two dimensions to align the laser beam on the optical axis, and a pair of lever members connected adjacent distal ends to the support base and pivotally mounted at the ends adjacent the respective actuator members.

19. The laser beam optical axis adjusting mechanism of claim 18 wherein the actuators are piezoelectric resistor elements.

20. The laser beam optical axis adjusting mechanism of claim 18 wherein the lever members are integrally connected to a support structure with L-shaped slits permitting movement.

21. The laser beam optical axis adjusting mechanism of claim 18 further including a base holding unit movably connecting the support base to permit the lever members to rotate the support base about the base holding unit.

22. The laser beam optical axis adjusting mechanism of claim 21 wherein the base holding unit has a conical end and the support base has a receptacle for receiving the conical end.

23. The laser beam optical axis adjusting mechanism of claim 21 wherein the base holding unit has a spherical end and the support base has a receptacle for receiving the spherical end.

24. The laser beam optical axis adjusting mechanism of claim 18 further including a controller for automatically driving the actuator unit to align the laser beam with an optical axis.

* * * * *